United States Patent [19]

Colella et al.

[11] Patent Number: 5,124,443

[45] Date of Patent: Jun. 23, 1992

[54] CDNA CLONES ENCODING CHICKEN EGG WHITE CYSTATIN

[75] Inventors: Rita Colella, Parlin; John W. C. Bird, Piscataway, both of N.J.; Hideaki Nagase, Fairway, Kans.

[73] Assignees: University of Kansas, Kansas City, Kans.; Rutgers, The State University of New Jersey, New Brunswick, N.J.

[21] Appl. No.: 352,736

[22] Filed: May 16, 1989

[51] Int. Cl.$^5$ .................... C07H 17/00; C12Q 1/68; C12P 21/06

[52] U.S. Cl. ........................ 536/27; 435/6; 435/69.1; 435/320.1

[58] Field of Search ................. 536/27; 435/6, 69.1, 435/320.1

[56] References Cited

PUBLICATIONS

Rita Coléila et al., "Chicken Egg White Crystatin" J. Biol. Chem. 264(29): 17164–17169, 1989.
Sen, L. C., et al. (1973) Archives of Biochem. and Biophysics. vol. 158, pp. 623–632.
Anastasi, A., et al. (1983) Biochem. J. vol. 211, pp. 129–138.
Schwabe, C., et al. (1984) Biochem. J. vol. 217, pp. 813–817.
Muller-Esterl, W., et al. (1985) FEBS Letters, vol. 191, No. 2 pp. 221–226.
"Nomenclature and classification of the proteins homologous with the cysteine-proteinase inhibitor checiken cystatin" BJ Letters, p. 312.
Ohkubo, I., et al. (1984) Biochemistry vol. 23, pp. 5691–5697.
Sueyoshi, T., et al. (Mar. 1985) FEBS 2347, vol. 182, No. 1 pp. 193–195.
Salvesen, G., et al. (1986) Biochem. J. vol. 234, pp. 429–434.
Gubler, U., et al. (1983) Gene. vol. 25, pp. 263–269.
Sanger, F., et al. (1977) Proc. Natl. Acad. Sci. USA vol. 74, No. 12, pp. 5463–5467.
Thomas, P. S. (1980) Proc. Natl. Acad. Sci. USA. vol. 77, No. 9, pp. 5201–5205.
Nagase, H., et al. (1981) The Journal of Biological Chemistry vol. 256, No. 23, pp. 11951–11954.
Fraker, P. J., et al. (1978) Biochemical and Biophysical Research Communications vol. 80, No. 4, pp. 849–857.
Okada, Y., et al. (1986) The Journal of Biological Chemistry vol. 261, No. 30, pp. 14245–14255.
Kozak, M. (1981) Nucleic Acids Research vol. 9, No. 20, pp. 5233–5249.
Abrahamson, M., et al. (1987) FEB 04763 vol. 216, No. 2, pp. 229–233.
Saitoh, et al. (1987) Gene. vol. 61, pp. 329–338.
Al-Hashimi, I., et al. (1988) The Journal of Biological Chemistry, vol. 263, No. 19, pp. 9381–9387.
Shaw, P. A., et al. (1988) The Journal of Biological Chemistry, vol. 263, No. 34, pp. 18133–18137.
Abe, K., et al. (1987) The Journal of Biological Chemistry vol. 262, No. 35, pp. 16793–16797.
Kartasova, L, et al. (1987) Nucleic Acids Research vol. 15, No. 15, pp. 5945–5962.
Fong, D., et al. (1979) Proc. Natl. Acad. Sci. USA vol. 76, No. 12, pp. 6481–6485.
Birnstiel, M. L., (1985) Cell, vol. 41, pp. 349–359.
Shapiro, D. J., et al. (1985) Bioessays, vol. 6, pp. 221–226.
Segundo, B. S., et al. (1986) FEBS 3714, vol. 201, No. 2 pp. 251–256.
Suzuki, T., et al. (1986) Insect Biochem. vol. 16, No. 4 pp. 589–595.
Kirsehke, H., et al. (1983) Biochem J. vol. 214 pp. 871 877.
Chap 8 (1984), pp. 211–230 "Purification of Eukaryotic Messenger RNA" by Michael J. Clemens in Transcription and Translation, A Practical Approach, ed B. D. Hanes and S. J. Higgins IRL Press Oxford.
Maniatus et al. (1982) "Molecular Cloning: A Laboratory Manual" pp. 2.118–2.119, 5.68–5.69, 7.26–7.29, 17.14, 4.2 and 1.13.

*Primary Examiner*—John W. Rollins
*Attorney, Agent, or Firm*—Felfe & Lynch

[57] ABSTRACT cDNA clones coding for the chicken Cysteine proteinase inhibitor cystatin were found and isolated using for example a synthetic oligonucleotide probe corresponding to amino acids 81–90 of the cystatin sequence. This was used to screen a lambda gt 11 chicken oviduct cDNA library. A full length cystatin cDNA was also isolated.

6 Claims, 7 Drawing Sheets

FIG. 1b

```
                CCACTCCGCTCCGCAGCCTTAAAATGGCGGCCAGGCGTGTAGTGCG
                                                                       46
              -23                                                 -9
                M   A   G   A   R   G   C   V   V   L   L   A   A   A   L
GTGTGTGGAGCCATGGCAGGAGCTCGGGGTTGCGTAGTGCTGCTGGCCGCGGCCCTA
                                                                      103
 -8                        1                                           11
  M   L   V   G   A   V   L   G   S   E   D   R   S   R   L   L   G   A   P
ATGCTCGTCGGCGCTGTCCTGGGCAGCGAGGACCGCTCCCGGCTCCTGGGGGCTCCA
                                                                      160
 -12                                                                   30
  V   P   V   D   E   N   D   E   G   L   Q   R   A   L   Q   F   A   M   A
GTGCCTGTAGATGAGAACGACGAGGGCTTGCAACGGGCCCTGCAGTTCGCGATGGCC
                                                                      217
 31                                                                    48
  E   Y   N   R   A   S   N   D   K   Y   S   S   R   V   V   R   V   I   S
GAGTACAACAGGGCCAGCAACGATAAGTACTCCAGCCGGGTGGTGCGGGTCATCAGC
                                                                      274
 50                                                                    68
  A   K   R   Q   L   V   S   G   I   K   Y   I   L   Q   V   E   I   G   R
GCCAAGCGGCAGCTCGTGTCTGGAATCAAGTACATCCTGCAGGTTGAGATTGGTCGC
                                                                      331
 69                                                                    87
  T   T   C   P   K   S   S   G   D   L   Q   S   C  *E   F   H   D   E   P
ACAACTTGCCCCAAGTCATCAGGTGATCTCCAGAGCTGCGAATTCCACGATGAGCCA
                                                                      388
 88                                                                   106
  E   M   A   K   Y   T   T   C   T   F.  V   V   Y   S   I   P   W   L   N
GAGATGGCTAAGTATACCACATGCACCTTTGTAGTGTACAGTATTCCTTGGCTAAAC
                                                                      445
 107                             116
  Q   I   K   L   L   E   S   K   C   Q  STOP
CAAATTAAACTGCTGGAAAGCAAGTGCCAGTAAGCCTCTCTTGGCTCCAGCAGTGAC
                                                                      502
CAGCAACCAGTTACTTGGAGGAAAAAAGAAGCAATAACATGAATTGAGATGGATTGT
                                                                      559
ATCGCTGCCTGTTAACTCATACTTCTGTACGCTTGTGCTATGCAAGTAAAACTATGT
                                                                      616
AATCTTACTATAGAGCACAGTACGATCTCGACTTTATTTTTCCTCTTTGTAGTTATA
                                                                      673
                                                 (1)
TTTTTGGAGTAGCTGTTTGTCTTCTCGCAGCTTTCCCAATAAAGCAACTCCAGTGTC
                                                                      730
                                             (2)
AAATTAAATGAATTGTGTCCCTATAAGTGACTACTGTAAACATTAAAACTCAATTCA
                                                                      787
 792
TCATTAAAAAAAAAAAAAAA
```

FIG. 4a

```
chcys     19  E  G  L  Q  R  A  L  Q  F  A  M  A  E  Y  N  R   34
         182  GAGGGCTTGCAACGGGCCCTGCAGTTCGCGATGGCCGAGTACAACAGG  229
hucy SAI  22  E  W  V  Q  R  A  L  H  F  A  I  S  E  Y  N  K   37
          --  GAGtGggTaCAgCGtgCCCTtCACTTCGCcATcagCGAGTATAACAaG   --
hucyC     21  E  G  V  R  R  A  L  D  F  A  V  G  E  Y  N  K   36
         216  GAGGGtgTGCgGCGTgCGGCTGGAcTTtGCcGTcGGCGAGTACAACAaa  263
rtcyS     19  E  G  A  S  E  A  L  N  Y  A  V  N  E  Y  N  E   34
          97  GAaGGagcctcAgaaGCatTGAaAcTatGCtgTcaatGAGTAtAAtgaa  144
oryzacy   19  N  D  L  H  L  V  D  L  A  R  F  A  V  T  E  H   34
          55  aAcGaCcTccACCtcGtCgacCtcgcCcgctTcGCCgtcacGAgcac  102
hukin    154  P  D  L  E  P  I  L  R  H  G  I  Q  Y  F  N  N   169
         505  ccaGaCcTGgAgCccattCTGagacaCGgcATtcagtAcTtAACAac    552 chcys     35  A  S  N  D  K  Y  S  S  R  V  V  R  V  I  S  A   50
         230  GCCAGCAACGATAAGTACTCCAGCCGGGTCGTGCGGGTCATCAGCGCC   277
hucy SAI  38  A  T  K  D  D  Y  Y  R  R  P  L  R  V  L  R  A   53
          --  GCCAcCAAaGATGAcTACTaCAGaCGtccGCTGCGGGTacTaAGaGCC   --
hucyC     37  A  S  N  D  M  Y  H  S  R  A  L  Q  V  V  R  A   52
         264  GCCAGCAACGACATGTACcaCAGCCGCGCCCTGCAGGTTGtGCGCGCC  311
rtcyS     35  K  N  S  D  L  Y  L  S  R  V  V  E  V  K  D  V   50
         145  aagAaCAgtGActtGTACctgAGCCGTGTGGTGgaaGTgAaggatGtC  192
oryzacy   35  N  K  K  A  N  S  L  E  F  E  K  L  V  S  V      50
         103  aaCAagAAgGccAATTctctgctggaGtTcGaGaaGCTtgTgAGtGtg  150
hukin    170  N  T  Q  H  S  S  L  F  M  L  N  E  V  K  R  A   185
         553  aaCActcAacATtccTccCtCttCatGCTtaatgaaGTaAaacGgGCC  600
```

FIG. 4b

```
chcys    51  K R Q L V S G I K Y I L Q V E I   66
            AAGCGGCAGCTCGTGTCTGGAATCAAGTACATCCTGCAGGTTGAGATT  325
hucy SAI 54  R Q Q T V G G V N Y F F D V E V   69
            AgGCaaCAGAccCGTtgggGGggTgAATtACtTCtTCgAcGTaGAGgTg  —
hucyC    53  R K Q I V A G V N Y F L D V E L   68
            cgcaaGCAGAtCGTagCGTgggTgAACtACTtCTtGGAcGTgGAGcTg  359
rtcys    51  Q K Q V V A G T K F F F D V I L   66
            cAaaaGCAGgTgGTgGCTGGAAcCAAaTtttTCTtgAtGTgattcTa  240
oryzacy  51  K Q Q V V A G T L Y F T I E V   66
            AAGCAGCAagTtGTcgCTGGcACtttGTACtattTcacaaTTGAGgTg  198
hukin    186 Q R Q V V A G L N F R I T Y S I   201
            cAaaGaCAGgTgGGTgGCTGGAtTgAAcTttcgaaTtacctactcaATT  648 chcys    67  G R T T C P K S S G D L Q S C E   82
            GGTCGCACAACTTGCCCCAAGTCATCAGGTGATCTCCAGAGCTGCGAA  373
hucy SAI 70  G R T I C T K S Q P N L D T C A   85
            GGcCGaACcATaTGtACCAAGTCccagcccaActTggAcAcCTGtGcc  —
hucyC    69  G R T T C T K T Q P N L D N C P   84
            GGcCGaACCACgTGtACCAAGACCcAAGACCcagcccAActTggAcAaCTGCccc  407
rtcys    67  G K T I C L K T Q G D L T N C P   82
            GGcaaaACAATaTGTttGAAGaCAcagGGTGACtTgaccAaCTGtccc  288
oryzacy  67  K E G D A K K L Y E A K V W E K   82
            aaggaaggggaTgcCaagAAGctcTatGaaGcTaaggtctGggagaAA  246
hukin    202 V Q T N C S K E N F L F L T P D   217
            GtgCaaACgAaTTGttCCAAagagaatttTctgtTCttaActccaGAc  696
```

FIG. 4c

CDNA CLONES ENCODING CHICKEN EGG WHITE CYSTATIN

This work was supported in part with funds from NIH grants HD18796 and AR 39189 and NSF grant DMB 8812046. Thus the U.S. Government has certain rights in the invention.

SUMMARY

A lambda gt 11 chicken oviduct cDNA library was screened with a synthetic oligonucleotide corresponding to amino acids 81-90 of the sequence for the chicken cysteine proteinase inhibitor, cystatin. A first cDNA clone isolated had a 367 bp insert which contained a coding sequence for cystatin from amino acid 82 to the carboxyl end plus untranslated region and a poly (A)+ tail. A second clone had a 431 bp insert and was shown to utilize another polyadenylation signal located 55 nucleotides downstream from that of the original clone. Further screening of the chicken oviduct library yielded a full-length cystatin cDNA. Sequence analysis indicated that cystatin contains an $NH_2$-terminal extension of 23 amino acids which is probably a signal sequence. The cystatin cDNA hybridized to an mRNA of approximately 0.95 kb and was present in varying amounts in all chicken tissues examined. The highest concentration was found in the lungs. Gizzard, brain and heart contained lesser amounts of cystatin mRNA but considerably higher than oviduct. Among a limited number of embryonic tissues examined, significantly higher levels of the mRNA were found in liver and heart tissues when compared with the adult tissues. Cystatin mRNA was not detected in RNA isolated from laying hen liver. These results suggest that the expression of the chicken cystatin gene are tissue-dependent and under developmental control.

DESCRIPTION OF THE FIGURES

FIG. 4. Comparison of the chicken cystatin cDNA with cDNAs of other members of the cystatin superfamily. The comparisor begins with FIG. 4a, continues with FIG. 4b and ends with FIG. 4c. Sequence homologies between chicken cystatin (choys) and human salivary cystatin SA-I (hu cys SA-I), (20), human cystatin C (hu cys C) (18), rat cystatin S (rt cys S) (21), oryzacystatin (oryzacy) (22), and human kininogen domain two (hu kin) (24). Nucleotides homologous to chicken cystatin are indicated by capital letters. The amino acid residues are shown for reference. The sequences are numbered according to the published data.

DESCRIPTION

Figure 1A:
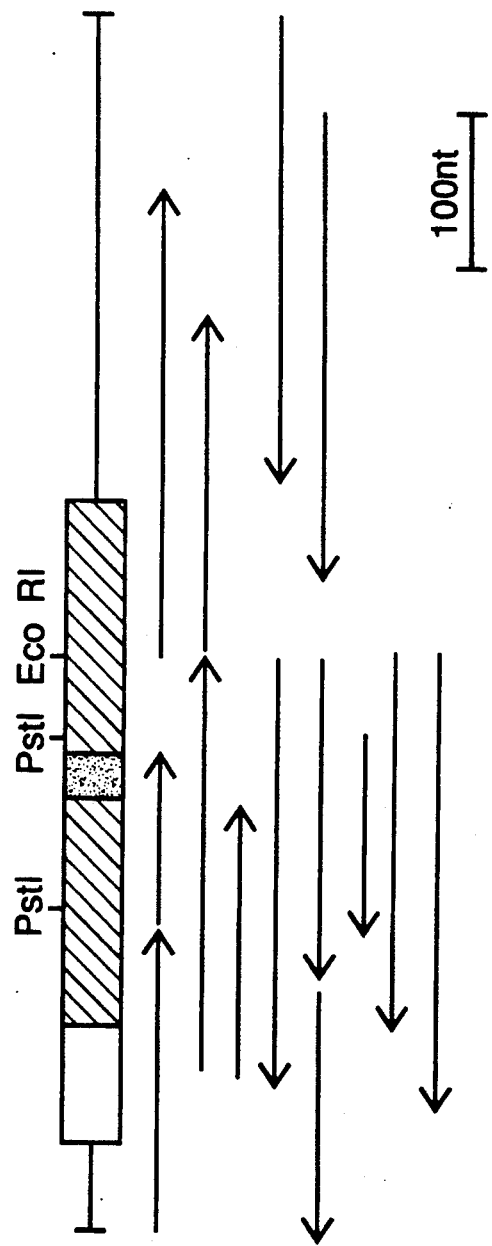
FIG. 1. Nucleotide and deduced amino acid sequence for chicken egg white cystatin. The sequencing strategy and position of the Pst I fragments used for subcloning are shown (1A). FIG. (1b) shows the sequence. The asterisk shows the start of the sequence for clones C2A and C10B. Both contained the coding sequence for cystatin from amino acid residue 82 to the carboxyl terminus and the 3' untranslated region. C2A had an insert of 367 bp and the first polyadenylation signal AATAAA (AAUAAA for RNA) located 14 bases upstream of the poly (A)+ tail (indicated by arrow). C10B contained a 431 bp insert with identical sequences as C2A but with an additional 62 bases at the 3' end. This area contained a second polyadenylation signal, AATTAAA (AAUUAAA for RNA), located 15 bases upstream of the poly (A)+ tail. Both putative polyadenylation signals are underlined. An internal Eco RI site is double underlined. Clone CYS13 contained the remaining 5' coding sequences for chicken cystatin including the Kozak initiation consensus sequence (underlined). Sequence analysis shows an $NH_2$-terminal extension for cystatin when compared to the known amino acid sequence (3).

An inhibitor of cysteine proteinases was first described in egg white by Sen and Whitaker (1) and was later called cystatin (2). Chicken egg white cystatin has a molecular weight of approximately 13,000 and binds tightly to papain-like cysteine proteinases (3). Inhibitors of cysteine proteinases with properties similar to chicken cystatin have been described in most cell types and biological fluids. Structural analysis of these inhibitors indicate that they belong to the cystatin superfamily, which is subdivided into three families (4,5).

Family one is known as the stefin family. Its members have $M_r$ of approximately 11,000, lack disulfide bonds and carbohydrates. They share one region of extended sequence homology with the other two families around the proposed reactive site. Members of this family are thought to represent the archtype of the superfamily. The second family members, the cystatins, have $M_r$ of approximately 13,000, contain two disulfide bonds but also lack carbohydrates. Members of this family share extended sequence homology to families one and three at the proposed reactive site and to family three at the carboxyl terminus.

The third family comprises the blood plasma kininogens which are larger than the members of the other two families. They were once known as high molecular weight cysteine proteinase inhibitors (6,7). Kininogens consist of three parts: a glycosylated $NH_2$-terminal heavy chain, the bradykinin moiety and a carboxyl terminal light chain. Cysteine proteinase inhibitory activity resides in the heavy chain whose structure is made up of three tandomly repeated cystatin-like domains, two of which are capable of inhibiting cystein proteinases (8). We describe herein the isolation of a cDNA encoding chicken egg white cystatin and its use to study the tissue distribution of its mRNA in adult and embryonic chicken tissue. Our data suggests that chicken cystatin expression is differentially regulated in different tissues. It forms the basis of further studies on the regulation of expression of the chicken cystatin gene and for a role for cystatin as a modulator of cysteine proteinase activities in physiological processes.

EXPERIMENTAL PROCEDURES

Materials. Reverse transcriptase from avian myeloblastosis virus was from Seikagagu America. Restriction endonucleases were purchased from International Biotechnology (New Haven, Conn.). Protein A-Sepharose CL-4B was purchased from Sigma (St. Louis, Mo.). [$^{35}$S]methionine and [$^{32}$P]dATP were from Amersham (Arlington Heights, Ill.). [$^{32}$P]dCTP was from New England Nuclear (Boston, Mass.). The Sequenase DNA sequencing kit was from U.S. Biochemicals. Rabbit reticulocyte lysate in vitro translation kit and pGEM 3 vector were from Promega. Purified chicken cystatin and chicken cystatin antibody were provided by Alan J. Barrett of Strangeways Research Laboratory, Cambridge, U.K.

Constructure of Chicken Oviduct cDNA Library. Total RNA from laying hen oviduct was prepared by the phenol/SDS method (9). Poly(A)+ RNA was isolated by oligo(dT)-cellulose chromatography (10). Double-stranded cDNA was synthesized according to Gubler and Hoffman (11) followed by Eco RI methylase and T4 DNA polymerase treatment. Methylated cDNA was ligated to Eco RI linkers. After the removal of linkers of Eco RI digestion, cDNA was size-fractionated by a Sepharose CL-4B column. Fractions larger than 500 base pairs were pooled and ligated to bacteriophage lambda gtII arms and packaged using the cell extracts obtained from Strategene. The library was amplified once in Y1090 (R−) cells. A portion of the library was kept at 4° C. with 0.5% chloroform and the rest stored at −70° C. with 7% dimethylsulfoxide.

Library Screening. Recombinant plaques were screened at a density of 50,000 plaques per 150 mm plate using a mixed synthetic oligonucleotide probe corresponding to cystatin's amino acid residues 81-90 (3). The sequence of the mixed oligonucleotide probe was

```
  81                              90
   C   E   F   H   D   E   P   E   M   A
5' TGT GAA TTT CAT GAT GAA CCT GAA ATG GC 3'
   C   G   C   C   C   G   C       G
                                A
                                G
```

This area was chosen because it showed the least codon degeneracy. The probe was end-labeled at the 5' end using standard procedures (10). The specific activity of the probe was estimated to be 2-10×10$^8$ cpm/ug. The filters were hybridized to the probe in a solution containing 50% formamide, 6x SSPE, 5X Denhardt's solution, 1% SDS and 100 ug/ml heat-denatured salmon sperm DNA at 42° C. for 24-36 hours. The filters were washed in 6x SSC, 0.1% SDS at 37° C. for 30 min with two changes of buffer followed by two additional washes in the same buffer at room temperature. The final wash consisted of a 20 min wash at room temperature in 2x SSC. The filters were autoradiographed at −70° C. for 2 days using intensifying screens.

Nucleic Acid Sequencing. DNA from positive phage was isolated by the plate lysate method described by Maniatus et al. (10). The DNA was digested with ECO RI endonuclease and the inserts subcloned into the Eco RI site of pGEM 3. Other subcloning vehicles include pUC 18, M13 and pETS. However, other vehicles for plasmid constructs are well known to those skilled in the art. Sequencing of both strands was done using the chain termination method of Sanger et al. (12). The cystatin cDNA was digested with Pst I and Pst I subfragments were also subcloned in the Pst I site of pGEM 3 for sequencing.

RNA Extraction and Northern Hybridization. Total RNA was extracted by the phenol/SDS method (9) from tissues of 11-day old chick embryos and from laying hens. Total RNA was denatured with formamide and electrophoresed on a 1% agarose-2.2M formaldehyde gel. RNA blot analysis was carried out by the method of Thomas (13). Filters were hybridized with nick-translated cDNA at 42° C. in 50% formamide, 1x Denhardt's solution, 5X SSPE and 150 ug/ml heat-denatured salmon sperm DNA. After hybridization the filters were washed four times in 2x SSC, 0.1% SDS for 20 min each time at 50° C. followed by a 20 min wash in 0.1x SSC at room temperature.

In Vitro Translation and Immunoprecipitation of Chicken Cystatin. Total RNA isolated from chicken oviduct was translated using the rabbit reticulocyte assay. The translated mixture was diluted four-fold in Tris buffer (30 mM Tris-HCl, pH 8.6/250 mM arginine/140 mM NaCl/ 1% Triton/ 6 mM EDTA/3 mM methionine/2 mM PMSF) (14) and preabsorbed to Protein A-Sepharose CL-4B to reduce non-specific binding of labeled proteins.

Chicken cystatin antibody (and pre-immune serum) were diluted ten-fold, complexed with Protein-A Sepharose CL-4B for one hour at room temperature and the beads were then washed 3x with Tris buffer. The diluted translation mixture was then added and allowed to bind to the cystatin antibody overnight at room temperature. The beads were washed 4x with Tris buffer followed by one wash with water. The antigen-antibody complex was dissociated by boiling for 5 minutes in SDS reducing buffer.

Iodination of Purified Egg White Cystatin. Purified chicken egg white cystatin was iodinated by the method of Fraker and Speck (15). After labeling the protein, free I. was removed by spin columns of Sephadex G-10 equilibrated with 50mM-Tris/HCl buffer, pH 7.5/0.15M NaCl/5mM CA$^{+2}$/0.05% Brij 35/0.02% NaN$_3$ as described previously (16).

Fluorography and Autoradiography. Immunoprecipitated products, translation products and $^{125}$I-labeled purified chicken cystatin were electrophoresed on SDS-polyacrylamide gel (10%) using the buffer system described by Nagase et al. (14). After electrophoresis, the proteins were stained and the gel soaked in DMSO twice for 30 minutes each time followed by soaking in 20%PPO/DMSO for 1 hour. The gel was then washed in H$_2$O, dried and autoradiographed for 2 weeks at −70° C.

DNA Sequence Analysis. The cDNA sequence coding for the full length cystatin protein was compared with known cDNA coding sequences for other members of the cystatin superfamily using the Microsoft Quickbasic Version 2.01 of Alan L. Goldin, Department of Biology, California Institute of Technology and the DNA Sequence Analysis System from International Biotechnologies (New Haven, Conn.).

EXAMPLE

Initial screening of the chicken oviduct cDNA library with the synthetic mixed oligonucleotide probes yielded two positive clones designated C2A and C10B. Both were subcloned into pGEM 3 and sequenced (FIG. 1). C2A contained an insert of 367 bases with coding sequences for cystatin from amino acid residue 82 to the carboxyl end plus 266 bases of 3' untranslated region. The polyadenylation signal AATAAA (AAUAAA in RNA) was present followed 14 bases later by a poly (A)+ tail. Clone C10B contained a 431 base insert with the same nucleotide sequence as clone C2A. However, the untranslated region contained an additional 62 bp at the 3' end and a less frequently used second polyadenylation signal, AATTAAA (AAUUAAA in RNA) (FIG. 1).

Figure 2:
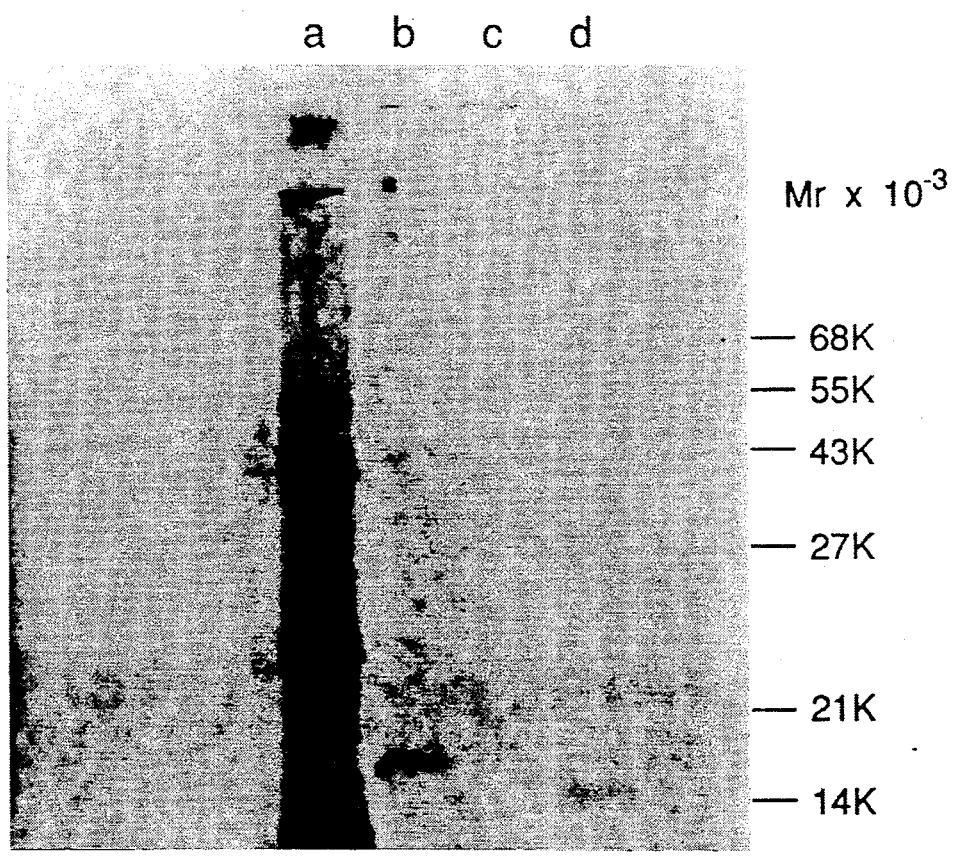
FIG. 2. Cell-free translation products of chicken cystatin. Hen oviduct RNA was translated using a rabbit reticulocyte translation system. Lane 1; total translation products of chicken oviduct RNA; lane 2; translation product immunoprecipitated with sheep anti-chicken cystatin serum; lane 3; translation products immunoprecipitated with sheep non-immune serum; lane 4: $1^{125}I$-labeled purified chicken egg white cystatin. Low molecular weight protein standards are indicated.

Insert C2A was labeled with $^{32}$P by nick translation and used to rescreen the library to obtain a full-length cystatin cDNA. Since both C2A and C10B contained coding sequences for cystatin from amino acid residue 82, the possibility of an internal Eco RI site at position 82-85 of the amino acid sequence was evident (FIG. 1). Therefore, a positive clone releasing two inserts after Eco RI digestion would be indicative of a full length cystatin cDNA. Two such clones were isolated, however, the cDNA inserts from both clones were larger than the cystatin mRNA of 0.95 kb (see below). Sequence data and Northern analysis indicated that they contained not only coding sequences for the mature cystatin protein and a part of a signal sequence but also sequences for an unrelated cDNA. It was concluded that these clones represent artifacts arising during construction of the cDNA library. Therefore, a Pst I fragment containing coding sequences for the proposed reactive site of cystatin (see FIG. 1) was used to rescreen the cDNA library for the remaining 5' sequences for chicken cystatin. A positive clone designated CYS-13 was isolated which released an insert of 376 bases with Eco RI digestion. This insert contained the remaining 5' coding sequences for the mature cystatin protein including the Kozak initiation consensus sequence (17). Sequence analysis from the postulated initiator methionine indicates a hydrophobic signal sequence of 23 amino acids residues with a calculated molecular weight of 2139 and a pI of 11.2. This suggests that egg white cystatin is synthesized as a precursor protein with a signal peptide of 23 amino acids residues which is removed during translocation. To confirm the presence of the signal peptide, chicken oviduct mRNA was translated in vitro using the rabbit reticulocyte lysate system without microsomal membranes. The translation product immunoprecipitated with anti-(chicken cystatin) IgG was identified to be 16,500 Da by SDS/PAGE, approximately 2,500 Da larger than purified chicken egg white cystatin (FIG. 2) which agrees with the calculated molecular weight of the signal peptide.

Figure 3:
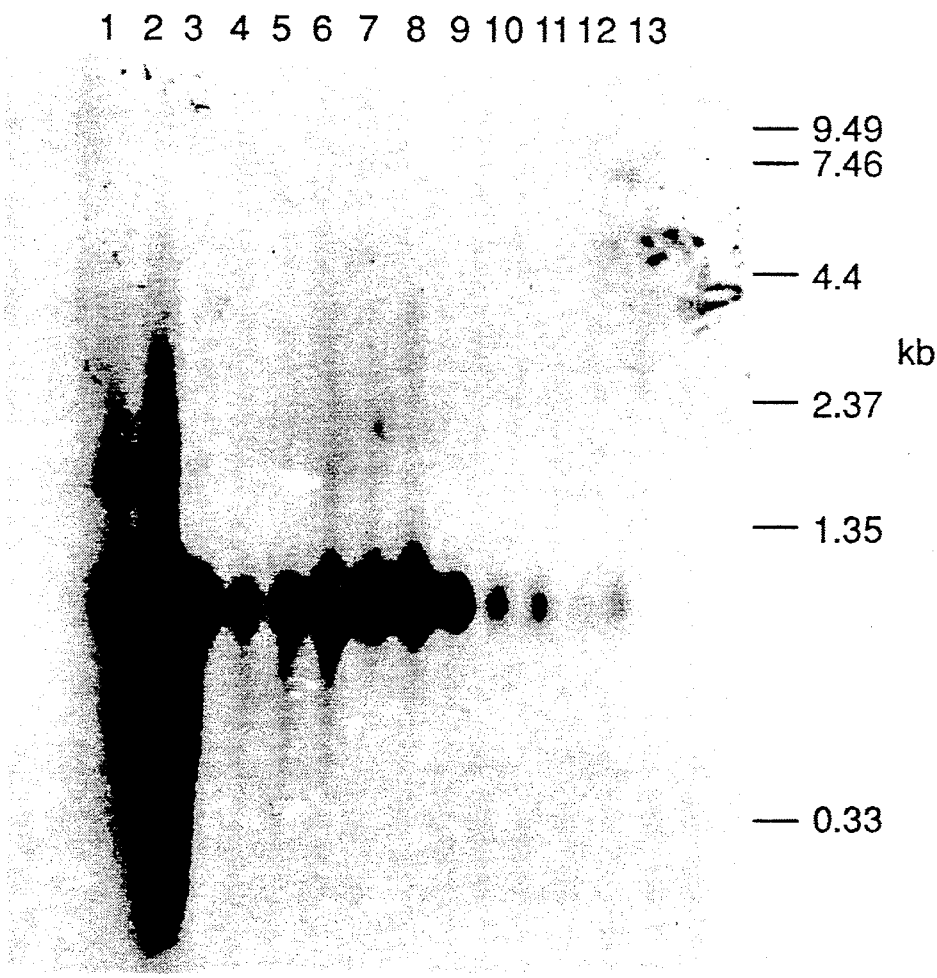
FIG. 3. Analysis of cystatin mRNA in various tissues. Total RNA (15 ug) from (1) gizzard, (2) lung, (3) small intestine, (4) oviduct, (5) heart, (6) embryonic heart, (7) brain, (8) embryonic brain, (9) leg muscle, (10) pectoral muscle, (11) embryonic pectoral muscle, (12) liver, and (13) embryonic liver was hybridized to insert C2A. RNA molecular markers are indicated.

Clone C2A was used as a probe for Northern analysis of cystatin mRNA in various tissues of the hen. This clone contains coding sequences for the carboxyl end of cystatin, an area which shows very little homology between stefins (family 1) and cystatins (family 2) (4). A message of approximately 0.95 kb was evident in RNA isolated from oviduct (FIG. 3, lane d). A message of similar size was also obtained when the Pst I fragment containing coding sequences for the proposed reactive site area was used as a probe.

Chicken cystatin mRNA was expressed in all adult tissues analyzed, the steady-state level being most abundant in lung (FIG. 3). Signal intensities of cystatin mRNA of gizzard, brain and heart followed that of lung in decreasing order. These tissues contained higher levels of mRNA than oviduct. The least amount was found in hen liver.

A limited number of embryonic tissues were also analyzed for cystatin mRNA steady-state levels and compared to the mRNA of the corresponding adult tissue. No apparent differences were seen between the signal intensities of cystatin mRNA of embryonic and adult brain or pectoral muscle. However, adult heart and liver had lower amounts of cystatin mRNA than the corresponding embryonic tissues (FIG. 3).

We have isolated a full length cDNA for chicken egg white cystatin from a chicken oviduct cDNA library. The amino acid sequence deduced from the nucleotide sequence is 100% in agreement with the published amino acid sequence of the purified egg white cystatin reported by Schwabe et al. (3), and contains a putative hydrophobic signal peptide of 23 amino acid residues. The cleavage site for the signal peptide is proposed to be between the gly residue at position −1 and the ser residue at position +1. Similar cleavage of a signal peptide after a glycine residue has also been reported for human cystatin C (18). Thus chicken egg white cystatin can be synthesized using this cDNA. The examples are illustrative of the invention. Thus other embodiments will be obvious to those skilled in the art. Thus human cDNA coding for cystatin or other mammalian or chordate species cDNA coding therefore can be isolated using similar or the same methods.

The presence of a signal sequence in chicken cystatin suggests that this protein exists predominantly in the extracellular space, as are most members of cystatin family two. A signal sequence for cystatin C and cystatins S and SN, three other members of this family, has also been reported (18-20).

Figure 4C:
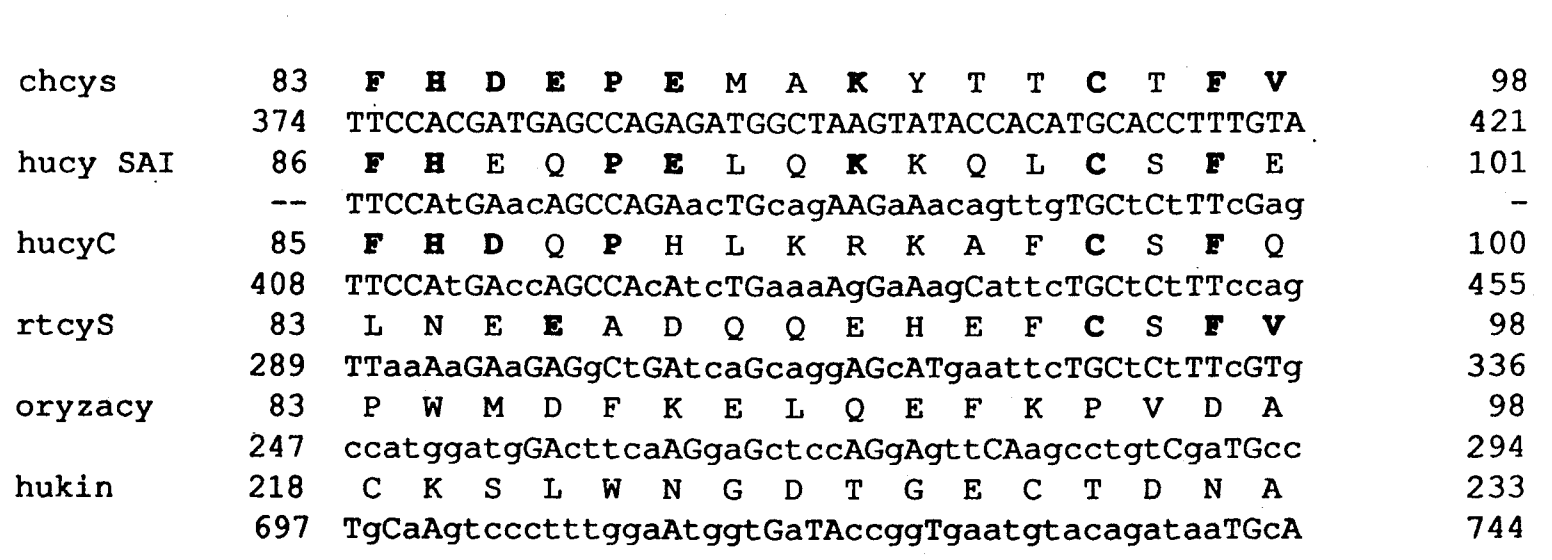

Comparison of the chicken cystatin cDNA sequence with those available for other members of the superfamily is shown in FIG. 4. The cDNAs with extended homology to the chicken cystatin cDNA included the cDNAs for human cystatin C (18), human salivary cystatin SA-I (20), and to a lesser extent, rat cystatin S (21), all members of cystatin family 2. The greatest percentage homology (60%-70% centered around the proposed reactive site region of all four molecules. Less extensive homology (54%) was found between the proposed reactive site of the rice cysteine proteinase inhibitor, orzycystatin (22) with chicken cystatin. The cDNA sequence reported for human stefin (23) had no apparent regions of similarity to chicken cystatin cDNA which may reflect the less extensive homology found between the amino acid sequences of these two proteins. Muller-Esterl et al. (4) reported only one region of moderate homology of the amino acid residues found around the proposed reactive site region of these two families.

The cDNA for the heavy chain of human kininogen (24) was also compared with the chicken cystatin cDNA. Comparison of the amino acid sequences of the two molecules showed two areas of homology of chicken cystatin with each of the three tandomly repeated cystatin-like domains of kininogen. These occur around the proposed reactive site residues and near the carboxyl terminus of the inhibitors (4). However, comparison of the cDNA sequences of the human kininogen with chicken cystatin showed only one region of homology around the proposed reactive site of the second cystatin-like domain of kininogen with that of chicken cystatin.

Sequence analysis of our cDNA clones indicates that there are two species of cystatin mRNA which utilize different polyadenylation signals. The commonly used consensus sequence AATAAA was found 14 bases upstream of the poly (A)+ tail in clone C2A. Clone 10B used the less common polyadenylation consensus sequence, AATTAAA, which was also reported to be the signal for polyadenylation of human salivary cystatin cDNA (19). The presence of more than one polyadenylation consensus sequence has been reported for other proteins by others (see ref. 25 for a review). In some cases, the choice of one poly (A)+ site over another correlates with the degree of stability of the mRNA (26). We do not know if the different mRNAs are preferentially expressed in different tissues since it was not possible to resolve the small differences in size in our Northern analysis. The significance of the two polyadenylation signals for egg white cystatin is yet to be resolved.

Northern analysis indicates that cystatin mRNA was present in all chicken tissues studied but showed variation in its steady-state level. The highest concentrations of cystatin mRNA were found in lung, gizzard, and brain in decreasing order, but was not expressed in high amounts in adult liver. We note that San Segundo et al. (27) found similar patterns of mRNA levels for the lysosomal cystein proteinase, cathepsin B, in rat tissues. The highest concentration of the cathepsin B mRNA was found in kidney followed by spleen, lung, brain, and heart. Liver cathepsin B mRNA was only 20% of the intensity of the signal found in kidney. Whether the expression of cysteine proteinase inhibitors is coregulated with the expression of the cysteins proteinases is a subject for study.

Although egg white, which is synthesized by the oviduct, has been a source for high concentrations of chicken cystatin; lung, gizzard, brain, heart and small intestine have higher cystatin mRNA levels than oviduct. It is possible that cystatin production by the oviduct correlates with the production of egg white and as such has a circadian component. We do not know at what stage of ovulation the hen was in when the oviduct tissue was removed for RNA extraction. The amount of cystatin mRNA during the various stages of egg production in the chicken remains to be investigated.

The size of chicken cystatin mRNA did not vary among the different tissues; in all instances a 0.95 kb message was noted. Therefore it is unlikely that the cystatin cDNA hybridizes to mRNAs coding for other members of the cystatin superfamily.

The high levels of expression of cystatin mRNA in embryonic heart and liver compared to the adult tissue suggests that cystatin may be hormonally or developmentally regulated in these tissues. A developmentally regulated cysteine proteinase inhibitor has been reported in the flesh fly, *Sarcophaga peregrina* (sarcocystatin) (28). The flesh fly undergoes distinct morphological changes during development which most likely involves proteolytic enzyme activity. Transient expression of another cysteine proteinase inhibitor, orzycystatin, has also been reported during the flowering of rice seeds (22). A cysteine proteinase inhibitor inducible by B-adrenergic agonists was isolated in rat submandibular glands and called rat cystatin S (21). The changes in cysteine proteinase inhibitor expression may reflect the regulation of cysteine proteinase activities that occurs during growth and morphological changes. Cysteine proteinase activity has been shown to be involved in the development of the cellular slime mold, *Diotyostelium discoidium* (29). Muscle cells in culture exhibit increased cysteine proteinase activity in parallel with the increased synthesis of muscle specific proteins during differentiation (30).

A role for cystatin has been the regulation of cysteine proteinase activity. The data presented show that chicken cystatin is not a ubiquitous protein but shows varying degrees of expression in different tissues and during different developmental stages. Thus the cystatin molecule may be useful to modify or change developmental or morphological changes in vivo. However, cystatin basically is useful in vitro as a cysteine proteinease inhibitor. The cDNA can be inserted into expression vectors known in the art which can then be made to synthesize the cystatin protein or its precursor. These vectors can be used to transfect cells such as a plant or an animal cell. The cell will then express cystatin protein as part of its phenotype. This may provide better growth through inhibition of protein degradation caused by cysteine proteineases, resistance to certain viral agents which use cysteine proteases to process their proteins, or protect crop plants from herbivores which utilize cysteine proteinases as important digestive enzymes C. A. Ryan, Bioassays 10:20–24 (1989). The cDNA for cystatin can have its bases changed and/or deleted to code for a protein with changes in its amino acid composition or sequence. Thus one can tailor a protein with altered specificity and activity of the inhibitor by changing the bases in the DNA code. Thus a group of cysteine proteinase inhibitors can be constructed.

The C2A, C10B and CYS-13 clones are on deposit at Rutgers University, Bureau of Biological Research, Nelson Laboratories, Bush Campus, P.O. Box 1059, Piscataway, N.J. 08855 and at the American Type Culture Collection ("ATCC"), 12301 Parklawn Drive, Rockville, Md. 20852. They were deposited at the ATCC on May 16, 1989. The deposit of clone C10B atcc designation 67986 includes the sequence for C2A as well. These clones are in a plasmid pGEM3 in a host cell HB10 (C10B) and DH5 (CYS-13)atcc designation 67985. The clones are also on deposit at the University of Kansas, Department of Biochemistry and Molecular Biology, 39th and Rainbow Blvd., Kansas City, Kans. 61103.

BIBLIOGRAPHY

1. Sen, L. C., and Whitaker, J. R. (1973) Arch. Biochem. Biophys. 158, 623–632
2. Anastasi, A., Brown, M., Kembhavi, A. A., Nioklin, M. J. H., Sayers, C. A., Sunter, D. C., and Barrett, A. J. (1983) Biochem. J. 211, 129–138
3. Schwabe, C., Anastasi, A., Crow, H., McDonald, J. K. and Barrett, A. J. (1984) Biochem. J. 217, 813–817
4. Muller-Esterl, W. Fritz, H, Kellermann, J, Lottspeich, F, Machleidt, W, and Turk, V. (1985) Febs Lett 191, 221–226
5. Barrett, A. J., Fritz, H, Grubb, A, Isemura, S, Jarvinen, M, Katunuma, N, Machleidt, W, Muller-Esterl, W, Sasaki, M, and Turk, V. (1985) Biochem J 236, 312.
6. Ohkubo, I, Kurachi, K, Takasawa, T, Shiokawa, H, and Sasaki, M. (1984) Biochemistry 23, 5691–5697
7. Sueyoshi, T, Enjyoji, K, Shimada, T, Kato, H, Iwanaga, S, Bando, Y, Kominami, E, and Katunuma, N. (1985) FEBS Lett 182, 193–195
8. Salvesin, G, Parkes, C, Abrahamson. M, Grubb, A and Barrett, A. J. (1985) Biochem J. 234, 429–434
9. Clemens, M. J. (1984) Purification of Eukaryotic Messenger RNA. In: *Transcription and Translation, A Practical Approach*. Edited by B. D. Hames and S. J. Higgins (IRL Press, Oxford) pp.211–230.

10. Maniatus, T., Fritsch, E. F. and Sambrook, J. (1982) *Molecular Coning: A Laboratory Manual* (Cold Spring Harbor, N.Y.)
11. Guber, U and Hoffman, B. J. (1983) Gene 25, 263-269
12. Sanger, F., Nicklen, S., and Coulson, A. R. (1977) Proc. Natl. Acad. Sci. USA 74, 5463-5467
13. Thomas, P. S. (1980) Proc. Natl. Acad. Sci. USA 77, 5201-5205
14. Nagase, H, Jackson, R. C., Brinckerhoff, C. E., Vater, C. A., and Harris, B. D. (1981) J Biol Chem 256, 11951-11954
15. Fraker, P. J. and Speck, J. C., Jr. (1978) Biochem Biophys Res Commun 80, 849-457
16. Okada, Y., Nagase, H., and Harris, E. D., Jr. (1986) J Biol Chem 261, 14245-14255
17. Kozak, M. (1981) Nucl Acad Res 9, 5233-5252
18. Abrahamson, M., Grubb, A., Olafeson, I., and Lundwall, A. (1987) Febs Lett. 216, 229-233
19. Saitoh, E., Kim, H. S. Smithies, O. and Maeda, N. (1987) Gene 61, 329-338.
20. Al-Hashimi, I, Dickinson, D. P. and Levine, M. J. (1988) J Biol Chem 263, 9381-9387
21. Shaw, P. A., Cox, J. L., Barka, T and Naito, Y. (1988) J Biol Chem 263, 18133-18137
22. Abe, K. Emori, Y, Kondo, H, Suzuki, K and Arai, S (1987) J Biol Chem 262, 16793-16797
23. Kartasova, P., Cornelissen, B. J. C., Belt, P., and van de Putte, P. (1987) Nucl Acids Res 15, 5945-5962
24. Ohkubo, I., Kurachi, K., Takasawa, T., Shiokawa, H., and Sasaki, M. (1984) Biochemistry 23, 5691-5697
25. Birnstiel, M. L., Busslinger, M. and Strub, K. (1986) Cell 41, 349-359
26. Shapiro, D. J., Blume, J. E., and Nielsen D. A. (1985) BioEssays 6, 221-226
27. San Segundo, B., Chan, S. J., and Steiner, D. F. (1986) Febs Lett 201, 251-256
28. Suzuki, T., and Natori, S. (1986) Insect Biochem 16, 589-595
29. Fong, D., and Bonner, J. T. (1979) Proc Natl Acad Sci USA 76, 6481-6485
30. Kirschke, H., Woods, L., Roisen, F. J., and Bird, J. W. C. (1983) Biochem. J. 214, 871-877

We claim:

1. A complete cDNA sequence inclusive of sequences coding for cystatin and its precursor consisting of

```
CCACTCCGCTCCGCAGCCTTAAAATGGCGGCC

AGGCGTGTAGTGCG
                                  46

-23
         M  A  G  A  R  G
GTGTGTGGAGCCATGGCAGGAGCTCGGGGTT

C  V  V  L  L  A  A  A  L
           GCGTAGTGCTGCTGGCCGCGGCCCTA
                                    103
 -8                             1
  M  L  V  G  A  V  L  G  S  E
ATGCTCGTCGGCGCTGTCCTGGGCAGCGAGG
                    |  |        |
                   120

11
           D  R  S  R  L  L  G  A  P
           ACCGCTCCCGGCTCCTGGGGGCTCCA
            |        |        |
                             160

12
          V  P  V  D  E  N  D  E  G  L
         GTGCCTGTAGATGAGAACGACGAGGGCTTGC
           |              |           |
          170            180

30
               Q  R  A  L  Q  F  A  M  A
               AACGGGCCCTGCAGTTCGCGATGGCC
                   |              |    217

31
  E  Y  N  R  A  S  N  D  K  Y
 GAGTACAACAGGGCCAGCAACGATAAGTACT
  |          |              |

49
              S  S  R  V  V  R  V  I  S
              CCAGCCGGGTGGTGCGGGTCATCAGC
               |           |           | 274
  50
   A  K  R  Q  L  V  S  G  I  K
   GCCAAGCGGCAGCTCGTGTCTGGAATCAAGT
    |              |           |

68
              Y  I  L  Q  V  E  I  G  R
              ACATCCTGCAGGTTGAGATTGGTCGC
               |              |      | 331
 69
  T  T  C  P  K  S  S  G  D  L
 ACAACTTGCCCCAAGTCATCAGGTGATCTCC
      |              |
     340

87
              Q  S  C  *E  F  H  D  E  P
              AGAGCTGCGAATTCCACGATGAGCCA
               |         |          | 388
 88
  E  M  A  K  Y  T  T  C  T  F
 GAGATGGCTAAGTATACCACATGCACCTTTG
  |              |              |

106
              V  V  Y  S  I  P  W  L  N
              TAGTGTACAGTATTCCTTGGCTAAAC
              ||           |           | 445

116
              Q  I  K  L  L  E  S  K  C  Q
              CAAATTAAACTGCTGGAAAGCAAGTGCCAG
                 |           |              |

STOP
              TAAGCCTCTCTTGGCTCCAGCAGTGAC
               |              |           | 502

CAGCAACCAGTTACTTGGAGGAAAAAGAAG

CAATAACATGAATTGAGATGGATTGT
                             |              |       559

ATCGCTGCCTGTTAACTCATACTTCTGTACG

CTTGTGCTATGCAAGTAAAACTATGT
                                                    619

AATCTTACTATAGAGCACAGTACGATCTCGA

CTTTATTTTTCCTCTTTGTAGTTATA
                                                    673
```

TTTTTGGAGTAGCTGTTTGTCTTCTCGCAGC (1)
TTTCCC<u>AATAAA</u>GCAACTCCAGTGTC
730

↓
AAATTAAATGAATTGTGTCCCTATAAGTGAC (2)
TACTGTAAAC<u>ATTAAA</u>ACTCAATTCA
787

792
TCAATTAAAAAAAAAAAAAAAA.

2. A cDNA for chicken egg white cystatin precursor.

3. The cDNA of chicken egg white cystatin in a cloning vehicle.

4. The cDNA of claim 3 in a cloning vehicle plasmid comprising pGEM3, pUC 18, M13 and pETS.

5. A method for cellular expression of chicken egg white cystatin or cystatin precursor protein comprising introducing the cDNA of claims 1, 2, 3 or 4 or derivatives thereof into plant or animal cells by means of a cloning vehicle or by means of insertion of said DNA into the cellular genome and expressing the protein or its precursor in the plant or animal cells.

6. A method for expressing chicken egg white cystatin or its precursor protein wherein the cDNA of claim 1, 2, 3 or 4 expresses the protein or its precursor comprising isolating mRNA coding for cystatin or its precursor using the cDNA of claim 1, 2 or 4 as a probe and expressing the mRNA in a eukaryotic or prokaryotic cell or cell-free system.

* * * * *

UNITED STATES PATENT AND TRADEMARK OFFICE
CERTIFICATE OF CORRECTION

PATENT NO. : 5,124,443
DATED      : June 23, 1992
INVENTOR(S) : Rita Colella, et al.

It is certified that error appears in the above-identified patent and that said Letters Patent is hereby corrected as shown below:

Col. 2, line 1:            change "lane 4:1$^{125}$I" to -- lane 4:$^{125}$I --.

Col. 2, line 3:            change "cvstatin" and insert -- cystatin --.

Col. 8, lines 34 and 36:   change "atcc" to -- ATCC --.

Col. 9, line 2:            change "Coning" and insert -- Cloning --.

Col. 10, line 50
     Claim 1:              Insert -- 107 -- above "CAAA"
                           to read as follows:

"    107
                                 Q
                                CAAA  ".

Signed and Sealed this

Eleventh Day of January, 1994

Attest:

BRUCE LEHMAN

*Attesting Officer*          *Commissioner of Patents and Trademarks*